United States Patent
Ganske et al.

(10) Patent No.: US 10,213,206 B2
(45) Date of Patent: Feb. 26, 2019

(54) GAS POWERED SYSTEM FOR PERFORMING REMOTE ISCHEMIC CONDITIONING

(71) Applicant: CellAegis Devices Inc., Mississauga (CA)

(72) Inventors: Rocky Eugene Ganske, Acton (CA); Raymond Cracauer, Beulah, CO (US); Lahav Gil, Toronto (CA)

(73) Assignee: CellAegis Devices Inc., Mississauga (CA)

( * ) Notice: Subject to any disclaimer, the term of this patent is extended or adjusted under 35 U.S.C. 154(b) by 369 days.

(21) Appl. No.: 14/774,009

(22) PCT Filed: Mar. 12, 2014

(86) PCT No.: PCT/IB2014/001424
§ 371 (c)(1),
(2) Date: Sep. 9, 2015

(87) PCT Pub. No.: WO2014/167422
PCT Pub. Date: Oct. 16, 2014

(65) Prior Publication Data
US 2016/0022269 A1    Jan. 28, 2016

Related U.S. Application Data

(60) Provisional application No. 61/789,919, filed on Mar. 15, 2013.

(51) Int. Cl.
*A61B 17/135* (2006.01)
*A61B 17/12* (2006.01)
(Continued)

(52) U.S. Cl.
CPC ............ *A61B 17/12* (2013.01); *A61B 17/135* (2013.01); *A61B 17/1355* (2013.01);
(Continued)

(58) Field of Classification Search
CPC ...... A61B 17/12; A61B 17/132; A61B 17/135; A61B 17/1355; A61B 2017/00548
See application file for complete search history.

(56) References Cited

U.S. PATENT DOCUMENTS

| 3,552,383 A | 1/1971 | Krueger et al. |
| 4,106,002 A | 8/1978 | Hogue, Jr. |

(Continued)

FOREIGN PATENT DOCUMENTS

| CN | 20109315 | 8/2008 |
| CN | 201098315 | 8/2008 |

(Continued)

OTHER PUBLICATIONS

Addison et al., "Noninvasive remote ischemic preconditioning for global protection of skeletal muscle against infarction," *Am. J. Physiol. Heart Circ. Physiol.*, vol. 285, pp. H1435-H1443 (2003).

(Continued)

*Primary Examiner* — Katherine Rodjom
(74) *Attorney, Agent, or Firm* — Wolf, Greenfield & Sacks, P.C.

(57) ABSTRACT

A device for performing a remote ischemic conditioning treatment. The device includes an inflatable cuff and a cartridge which is a source of gas for inflating the cuff. A first valve controls the flow of gas from the cartridge to the cuff so as to maintain a predetermined pressure in the cuff during an ischemic period. A second valve allows gas to escape from the cuff during a reperfusion period of the remote ischemic conditioning treatment. A controller which may be battery-powered is used to control the opening and closing of the valves. The cartridge may contain a gas, or materials which, under certain conditions, react to produce a gas. The chemical reaction may be initiated by an electrical pulse or signal from the controller.

22 Claims, 3 Drawing Sheets

(51) Int. Cl.
  *A61M 39/24* (2006.01)
  *A61M 39/22* (2006.01)
  *A61H 1/00* (2006.01)
  *A61B 17/00* (2006.01)
  *A61B 90/00* (2016.01)

(52) U.S. Cl.
  CPC ............ *A61H 1/008* (2013.01); *A61M 39/22* (2013.01); *A61M 39/24* (2013.01); *A61B 2017/00221* (2013.01); *A61B 2017/00548* (2013.01); *A61B 2017/00876* (2013.01); *A61B 2090/032* (2016.02); *A61B 2090/064* (2016.02); *A61H 2201/5097* (2013.01)

(56) References Cited

U.S. PATENT DOCUMENTS

| | | | |
|---|---|---|---|
| 4,206,764 | A | 6/1980 | Williams |
| 4,294,261 | A | 10/1981 | Baker et al. |
| 4,321,929 | A | 3/1982 | Lemelson et al. |
| 4,664,651 | A | 5/1987 | Weinshenker et al. |
| 4,690,151 | A | 9/1987 | Utsunomiya et al. |
| 4,967,758 | A | 11/1990 | Masciarotte |
| 5,072,736 | A | 12/1991 | Ogawa et al. |
| 5,135,003 | A | 8/1992 | Souma |
| 5,201,758 | A | 4/1993 | Glover |
| 5,267,565 | A | 12/1993 | Beard et al. |
| 5,569,304 | A | 10/1996 | Ulrich |
| 5,571,075 | A | 11/1996 | Bullard et al. |
| 5,634,467 | A | 6/1997 | Nevo |
| 5,643,315 | A | 7/1997 | Daneshvar |
| 5,651,369 | A | 7/1997 | Tomita |
| 5,687,732 | A | 11/1997 | Inagaki et al. |
| 6,152,881 | A | 11/2000 | Raines et al. |
| 6,210,423 | B1 | 4/2001 | Kim et al. |
| 6,245,023 | B1 | 6/2001 | Clemmons |
| 6,251,080 | B1 | 6/2001 | Henkin et al. |
| 6,344,025 | B1 | 2/2002 | Inagaki et al. |
| 6,485,429 | B2 | 11/2002 | Forstner |
| 6,550,482 | B1 | 4/2003 | Burbank et al. |
| 6,626,840 | B2 | 9/2003 | Drzewiecki et al. |
| 6,702,720 | B2 | 3/2004 | Dardik |
| 6,719,704 | B2 | 4/2004 | Narimatsu et al. |
| 6,858,012 | B2 | 2/2005 | Burns et al. |
| 6,905,456 | B1 | 6/2005 | Brunner et al. |
| 6,962,599 | B2 | 11/2005 | Hui et al. |
| 7,004,907 | B2 | 2/2006 | Banet et al. |
| 7,018,335 | B2 | 3/2006 | Kario et al. |
| 7,048,702 | B2 | 5/2006 | Hui |
| 7,111,346 | B2 | 9/2006 | Inman et al. |
| 7,166,077 | B2 | 1/2007 | Millay et al. |
| 7,228,576 | B2 | 6/2007 | Inman et al. |
| 7,314,478 | B2 | 1/2008 | Hui |
| 7,338,410 | B2 | 3/2008 | Dardik et al. |
| 7,374,540 | B2 | 5/2008 | Schnall et al. |
| 7,390,303 | B2 | 6/2008 | Dafni |
| 7,404,221 | B2 | 7/2008 | Sackner |
| 7,427,268 | B2 | 9/2008 | Millay et al. |
| 7,485,131 | B2 | 2/2009 | Hovanes et al. |
| 7,517,312 | B2 | 4/2009 | Loeb et al. |
| 7,689,286 | B2 | 3/2010 | Pastore et al. |
| 7,717,855 | B2 | 5/2010 | Caldarone et al. |
| 7,885,710 | B2 | 2/2011 | Sih et al. |
| 8,114,026 | B2 | 2/2012 | Leschinsky |
| 8,246,548 | B2 | 8/2012 | Naghavi |
| 8,764,789 | B2 | 7/2014 | Ganske et al. |
| 8,790,266 | B2 | 7/2014 | Caldarone et al. |
| 8,911,469 | B2 | 12/2014 | Raheman |
| 2001/0029389 | A1 | 10/2001 | Kim et al. |
| 2003/0013974 | A1 | 1/2003 | Natarajan et al. |
| 2003/0065270 | A1 | 4/2003 | Raines et al. |
| 2003/0176795 | A1 | 9/2003 | Harris et al. |
| 2003/0216651 | A1 | 11/2003 | Burns et al. |
| 2003/0233118 | A1 | 12/2003 | Hui |
| 2004/0044290 | A1 | 3/2004 | Ward et al. |
| 2004/0064076 | A1 | 4/2004 | Bilgi et al. |
| 2004/0102818 | A1 | 5/2004 | Hakky et al. |
| 2004/0241634 | A1 | 12/2004 | Millis et al. |
| 2004/0255956 | A1 | 12/2004 | Vinten-Johansen |
| 2005/0004476 | A1 | 1/2005 | Payvar et al. |
| 2005/0070405 | A1 | 3/2005 | Egger |
| 2005/0159640 | A1 | 7/2005 | Barbut et al. |
| 2005/0171444 | A1 | 8/2005 | Ono et al. |
| 2005/0177078 | A1 | 8/2005 | Loeb et al. |
| 2006/0052712 | A1 | 3/2006 | Poliac et al. |
| 2006/0052713 | A1 | 3/2006 | Poliac et al. |
| 2006/0052714 | A1 | 3/2006 | Poliac et al. |
| 2006/0058717 | A1 | 3/2006 | Hui et al. |
| 2006/0100639 | A1 | 5/2006 | Levin et al. |
| 2006/0142663 | A1 | 6/2006 | Sawanoi et al. |
| 2007/0005106 | A1 | 1/2007 | Adducci |
| 2007/0055188 | A1 | 3/2007 | Avni et al. |
| 2007/0135836 | A1 | 6/2007 | McEwen et al. |
| 2007/0150005 | A1 | 6/2007 | Sih et al. |
| 2007/0247304 | A1 | 10/2007 | Bonnefin et al. |
| 2008/0077176 | A1 | 3/2008 | Hanlon et al. |
| 2008/0139949 | A1 | 6/2008 | Caldarone et al. |
| 2008/0222769 | A1 | 9/2008 | Natonson et al. |
| 2009/0036785 | A1 | 2/2009 | Danielson |
| 2009/0124912 | A1 | 5/2009 | McEwen et al. |
| 2009/0137884 | A1 | 5/2009 | Naghavi et al. |
| 2009/0287069 | A1 | 11/2009 | Naghavi et al. |
| 2009/0318818 | A1 | 12/2009 | Whitaker et al. |
| 2009/0324748 | A1 | 12/2009 | Dobson |
| 2010/0081941 | A1 | 4/2010 | Naghavi et al. |
| 2010/0081977 | A1 | 4/2010 | Vess |
| 2010/0105993 | A1 | 4/2010 | Naghavi et al. |
| 2010/0160799 | A1 | 6/2010 | Caldarone et al. |
| 2010/0185220 | A1 | 7/2010 | Naghavi et al. |
| 2010/0186752 | A1 | 7/2010 | Rixson |
| 2010/0268130 | A1 | 10/2010 | Khan |
| 2010/0292619 | A1 | 11/2010 | Redington et al. |
| 2010/0305607 | A1 | 12/2010 | Caldarone et al. |
| 2010/0322467 | A1 | 12/2010 | Reed et al. |
| 2010/0324429 | A1* | 12/2010 | Leschinsky ........ A61B 5/02208 600/493 |
| 2010/0326442 | A1 | 12/2010 | Hamilton et al. |
| 2010/0328142 | A1 | 12/2010 | Zoughi et al. |
| 2011/0077566 | A1 | 3/2011 | Ganapathy |
| 2011/0127881 | A1* | 6/2011 | Howarth ............... H01L 41/113 310/319 |
| 2011/0152650 | A1* | 6/2011 | Donehoo ........... A61B 5/02141 600/324 |
| 2011/0190807 | A1 | 8/2011 | Redington et al. |
| 2011/0238107 | A1 | 9/2011 | Raheman |
| 2011/0240043 | A1 | 10/2011 | Redington |
| 2011/0251635 | A1 | 10/2011 | Caldarone |
| 2012/0130419 | A1 | 5/2012 | Leschinsky |
| 2012/0277789 | A1 | 11/2012 | Caldarone et al. |
| 2013/0317581 | A1 | 11/2013 | Redington |
| 2014/0024986 | A1 | 1/2014 | Souma |
| 2014/0296756 | A1 | 10/2014 | Ganske et al. |

FOREIGN PATENT DOCUMENTS

| | | |
|---|---|---|
| CN | 101317805 | 12/2008 |
| CN | 201316381 | 9/2009 |
| EP | 0 960 598 | 12/1999 |
| EP | 1 016 379 | 5/2000 |
| EP | 1 249 218 | 10/2002 |
| EP | 2 168 553 | 3/2010 |
| EP | 2 301 496 | 3/2011 |
| GB | 1 323 365 | 7/1973 |
| JP | 2001221 | 1/1990 |
| JP | 07-051276 | 2/1995 |
| JP | 2001505472 | 4/2001 |
| JP | 2002539879 | 11/2002 |
| RU | 2 253 429 | 6/2005 |
| WO | WO 83/00995 | 3/1983 |
| WO | WO 91/18571 | 12/1990 |
| WO | WO 98/30144 | 7/1998 |
| WO | WO 00/57776 | 10/2000 |
| WO | WO 2005/011503 | 2/2005 |
| WO | WO 2005/051250 | 6/2005 |

(56) References Cited

FOREIGN PATENT DOCUMENTS

| | | |
|---|---|---|
| WO | WO 2005/077265 | 8/2005 |
| WO | WO 2006/024871 | 3/2006 |
| WO | WO 2006/030441 | 3/2006 |
| WO | WO 2006/061825 | 6/2006 |
| WO | WO 2007/085816 | 8/2007 |
| WO | WO 2007/085828 | 8/2007 |
| WO | WO 2007/087707 | 8/2007 |
| WO | WO 2008/148045 | 12/2008 |
| WO | WO 2008/148062 | 12/2008 |
| WO | WO 2009/049103 | 4/2009 |
| WO | WO 2010/132115 | 11/2010 |
| WO | WO 2011/005538 | 1/2011 |
| WO | WO 2011/127341 | 10/2011 |
| WO | WO 2012/024342 | 2/2012 |
| WO | WO 2012/132268 | 10/2012 |
| WO | WO 2012/142360 | 10/2012 |

OTHER PUBLICATIONS

Ali et al. Remote ischemic preconditioning reduces myocardial and renal injury after elective abdominal aortic aneurysm repair: a randomized controlled trial,: *Circulation*, vol. 116, 11 Suppl., pp. I-98-I-105 (Sep. 2007).
Bartekova et al., "Liver ischemia induced remote preconditioning: role of cardioprotective proteins," Abstracts from the 25th Annual Scientific Sessions, European Section of the International Society for Heart Research, 2 pages (Jun. 21-25, 2005).
Botker et al., "Upper-limb ischemia during ambulance transfer reduces myocardial perfusion injury in STEMI," Heartwire (Mar. 28, 2009) Featured at i2 Session of AAC. Mar. 28-31, 2009 (accessed on Mar. 5, 2012 from http://www.theheart.org/article/951627.do).
Botker et al., Remote ischaemic conditioning before hospital admission, as a complement to angioplasty, and effect on myocardial salvage in patients with acute myocardial infarction: a randomised trial, *Lancet*, vol. 375, Issue No. 9716, pp. 727-734 (Feb. 2010).
Brzozowski et al., "Ischemic preconditioning of remote organs attenuates gastric ischemia—reperfusion injury through involvement of prostaglandins and sensory nerves," *Eur. J. Pharmacol.*, vol. 499, Issue Nos. 1-2, pp. 201-213 (Sep. 2004).
Cheung et al., "Randomized controlled trial of the effects of remote ischemic preconditioning on children undergoing cardiac surgery: first clinical application in humans," *J. Am. Coll. Cardiol.*, vol. 47, Issue No. 11, pp. 2277-2282 (Jun. 2006).
M. Ebbinghaus, Examiner European Patent Office, Supplementary Partial European Search Report—Application No. 14783205.9, dated Apr. 25, 2017, 7 pages.
Dickson et al., "Rabbit heart can be "preconditioned" via transfer of coronary effluent," *Am. J. Physiol.*, vol. 277, Issue No. 6, Pt. 2, pp. H2451-H2457 (Dec. 1999).
Dong et al., "Limb ischemic preconditioning reduces infarct size following myocardial ischemia-reperfusion in rats," vol. 56, Issue No. 1, pp. 41-46 (Feb. 2004) [Chinese].
Dong et al., "Limb ischemic preconditioning reduces infarct size following myocardial ischemia-reperfusion in rats," vol. 56, Issue No. 1, pp. 41-46 (Feb. 2004) [English abstract].
Gho et al., "Myocardial protection by brief ischemia in noncardiac tissue," *Circulation*, vol. 94, Issue No. 9, pp. 2193-2200 (Nov. 1996).
Hausenloy et al., "Effect of remote ischaemic preconditioning on myocardial injury in patients undergoing coronary artery bypass graft surgery: a randomised controlled trial," *Lancet*, vol. 370, Issue No. 9587, pp. 575-579 (Aug. 2007).
Hausenloy et al., "Preconditioning and postconditioning: underlying mechanisms and clinical application," *Atherosclerosis*, vol. 204, Issue No. 2, pp. 334-341 (Jun. 2009).
Hausenloy et al., "The therapeutic potential of ischemic conditioning: an update," *Nat. Rev. Cardiol.*, vol. 8, Issue No. 11, pp. 619-629 (Jun. 2011).
Hoole et al., "Cardiac Remote Ischemic Preconditioning in Coronary Stenting (CRISP Stent) Study: a prospective, randomized control trial" *Circulation*, vol. 119, Issue No. 6, pp. 820-827 (Feb. 2009).
Jenkins et al., "Ischaemic preconditioning reduces troponin T release in patients undergoing coronary artery bypass surgery," *Heart*, vol. 77, Issue No. 4, pp. 314-318 (Apr. 1997).
Kharbanda et al., "Ischemic preconditioning prevents endothelial injury and systemic neutrophil activation during ischemia-reperfusion in humans in vivo," *Circulation*, vol. 103, Issue No. 12, pp. 1624-1630 (Mar. 2001).
Kharbanda et al., "Remote ischaemic preconditioning protects against cardiopulmonary bypass-induced tissue injury: a preclinical study," *Heart*, vol. 92, Issue No. 10, pp. 1506-1511 (Eur. Pub—Jul. 2006).
Kharbanda et al., "Translation of remote ischaemic preconditioning into clinical practice," *Lancet*, vol. 374, Issue No. 9700, pp. 1557-1565 (Oct. 2009).
Kharbanda et al., "Transient limb ischemia induces remote ischemic preconditioning in vivo," *Circulation*, vol. 106, Issue No. 23, pp. 2881-2883 (Dec. 2002).
Konstantinov et al., "Remote ischemic preconditioning of the recipient reduces myocardial ischemia-reperfusion injury of the denervated donor heart via a Katp channel-dependent mechanism," *Transplantation*, vol. 79, Issue No. 12, pp. 1691-1695 (Jun. 2005).
Konstantinov et al., "The remote ischemic preconditioning stimulus modifies inflammatory gene expression in humans," *Physiol Genomics*, vol. 19, No. 1, pp. 143-150 (Sep. 2004).
Konstantinov et al., "The remote ischemic preconditioning stimulus modifies gene expression in mouse myocardium," *J. Thorac. Cardiovasc. Surg.*, vol. 130, Issue No. 5, pp. 1326-1332 (Nov. 2005).
Lang et al., "Myocardial preconditioning and remote renal factor preconditioning—identifying a protective.using proteomic methods?," *Basic Res. Cardiol.*, vol. 101, Issue No. 2, pp. 149-158 (Mar. 2006).
Laskey et al., "Frequency and clinical significance of ischemic preconditioning during percutaneous coronary intervention," *J. Am. Coll. Cardiol.*, vol. 24, Issue No. 6, pp. 998-1003 (Sep. 2003).
Leesar et al., "Nonelectrocardiographic evidence that both ischemic preconditioning and adenosine preconditioning exist in humans," *J. Am. Coll. Cardiol.*, vol. 42, Issue No. 3, pp. 437-435 (Aug. 2003).
Leesar et al., "Preconditioning of human myocardium with adenosine during coronary angioplasty," *Circulation*, vol. 95, Issue No. 11, pp. 2500-2507 (Jun. 1997).
Loukogeorgakis et al., "Remote ischemic preconditioning provides early and late protection against endothelial ischemia-reperfusion injury in humans: role of the autonomic nervous system," *J. Am. Coll. Cardiol.*, vol. 46, Issue No. 3, pp. 450-456 (Aug. 2005).
Loukogeorgakis et al., "Transient limb ischemia induces remote preconditioning and remote postconditioning in humans by a K(ATP)-channel dependent mechanism," *Circulation*, vol. 116, Issue No. 12, pp. 1386-1395 (Sep. 2007).
McCully et al., "Adenosine-enhanced ischemic preconditioning: adenosine receptor involvement during ischemia and reperfusion," *Am. J. Physiol. Heart Circ. Physiol.*, vol. 280, Issue No. 2, pp. H591-H602 (Feb. 2001).
Murray et al., "Preconditioning with ischemia: a delay of lethal cell injury in ischemic myocardium," *Circulation*, vol. 74, Issue No. 5, pp. 1124-1136 (Nov. 1986).
Nandagopal et al., "Critical role for nitric oxide signaling in cardiac and neuronal ischemic preconditioning and tolerance," *J. Pharmacol. Exp. Ther.*, vol. 297, Issue No. 2, pp. 474-478 (May 2001).
Peng et al., "The protective effects of ischemic and calcitonin gene-related peptide-induced preconditioning on myocardial injury by endothelin-1 in the isolated perfused rat heart," *Life Sci.*, vol. 59, Issue No. 18, pp. 1507-1514 (1996).
Penttila et al., "Ischemic preconditioning does not improve myocardial preservation during off-pump multivessel coronary operation," *Ann. Thorac. Surg.*, vol. 75, Issue No. 4, pp. 1246-1252 (Apr. 2003).

(56) References Cited

OTHER PUBLICATIONS

Peralta et al., "Liver ischemic preconditioning: a new strategy for the prevention of ischemia-reperfusion injury," *Transplant Proc.*, vol. 35, Issue No. 5, pp. 1800-1802 (Aug. 2003).

Przyklenk et al., "Regional ischemic 'preconditioning' protects remote virgin myocardium from subsequent sustained coronary occlusion," *Circulation*, vol. 87, Issue No. 3, pp. 893-899 (Mar. 1993).

Redington et al., "Exploring remote ischaemic preconditioning," *Internal Innovation*, pp. 42-44 www.research.media.eu.

Saxena et al., "Remote ischemic conditioning: evolution of the concept, mechanisms, and clinical application," *J. Card. Surg.*, vol. 25, Issue No. 1, pp. 127-134 (Jan.-Feb. 2010).

Schmidt et al., "Intermittent peripheral tissue ischemia during coronary ischemia reduces myocardial infarction through a KATP-dependent mechanism: first demonstration of remote ischemic preconditioning," *Am. J. Physiol. Heart Circ. Physiol.*, vol. 292, Issue No. 4, pp. H1883-H1890 (Apr. 2007).

Schoemaker et al., "Bradykinin mediates cardiac preconditioning at a distance," *Am. J. Physiol. Heart Circ. Physiol.*, vol. 278, Issue No. 5, pp. H1571-H1576 (May 2000).

Takarada et al., "Applications of vascular occlusion diminish disuse atrophy of knee extensor muscles," *ed. Sci. Sports. Exerc.*, vol. 32, Issue No. 12, pp. 2035-2039 (Dec. 2000).

Tanaka et al., "Expression of heat shock protein after ischemic preconditioning in rabbit hearts," *Jpn. Circ J.*, vol. 62, Issue No. 7, pp. 512-516 (Jul. 1998).

Tejwani et al., "Tourniquet cuff pressure: The gulf between science and practice," *J. Trauma*, vol. 61, Issue No. 6, pp. 1415-1418 (Dec. 2006) [Abstract only].

Tomai et al., "Ischemic preconditioning in humans: models, mediators, and clinical relevance," *Circulation*, vol. 100, Issue No. 5, pp. 559-563 (Aug. 1999).

Wolfrum et al., "Calcitonin gene related peptide mediates cardioprotection by remote preconditioning," *Regul. Pept.*, vol. 127, Issue Nos. 1-3, pp. 217-224 (Apr. 2005).

Alison Canteenwalla, Authorized officer Canadian Intellectual Property Office, International Search Report—Application No. PCT/IB2014/001424, dated Nov. 24, 2014, 9 pages, *together with the Written Opinion of the International Searching Authority*.

William Byrne, Authorized officer The International Bureau of WIPO, International Preliminary Report on Patentability—Application No. PCT/IB2014/001424, dated May 11, 2015, 6 pages.

\* cited by examiner

GAS POWERED SYSTEM FOR PERFORMING REMOTE ISCHEMIC CONDITIONING

RELATED APPLICATIONS

This application claims the benefit under 35 U.S.C. § 119(e) of U.S. Provisional Application No. 61/789,919, filed Mar. 15, 2013, and entitled "GAS POWERED SYSTEM FOR PERFORMING REMOTE ISCHEMIC CONDITIONING," the entire contents of which are incorporated herein by reference.

FIELD

This invention relates generally to systems for performing remote ischemic conditioning, and more particularly, to a gas-powered system for performing remote ischemic conditioning.

BACKGROUND

Ischemic diseases are significant causes of mortality in industrialized nations. It is well established that tissue damage results from ischemia (insufficient blood flow to a tissue) followed by reperfusion (reflow of blood to the tissue). Ischemia and reperfusion cause disturbance of microcirculation with ensuing tissue damage and organ dysfunction. Organs such as the kidney, heart, liver, pancreas, lung, brain and intestine are known to sustain damage following ischemia and reperfusion.

In ischemic conditioning (IC), a tissue or organ or region of a subject's body is deliberately subjected to brief ischemic episodes, followed by brief reperfusion episodes. IC has been found to render the tissue, organ or region resistant to injury during subsequent ischemic episodes. The phenomenon of ischemic conditioning has been demonstrated in most mammalian tissues. IC is now recognized as one of the most potent innate protective mechanisms against ischemia-reperfusion (I-R) injury. IC has also been shown to improve athletic performance, to treat and prevent restenosis, to reduce heart dysfunction or failure after myocardial infarction, and to treat traumatic injury. IC may be performed prior to (pre-), during (per-) and/or following (post-) an ischemic injury or other injury which benefits from IC.

Remote ischemic conditioning (RIC), as used herein, refers to a non-invasive process of deliberately inducing an ischemic event or period (typically by occluding arterial blood flow) followed by a reperfusion event or period (typically where blood is allowed to reperfuse) that is typically performed on an upper or lower limb or on a region of the body that is remote from an organ or tissue that is intended to benefit from the process itself. RIC may be contrasted with local IC which involves blood flow occlusion and reperfusion in a tissue or organ or region of the body to be protected from an existing or a future anticipated ischemia/reperfusion injury and is typically an invasive procedure. An example is local IC of the heart prior to cardiac surgery.

RIC may be performed as a single cycle (i.e., one ischemic event followed by one reperfusion event) or as multiple cycles. Multiple cycles include but are not limited to two, three, four, five or more cycles. The one or multiple cycles, when performed consecutively without significant delay, are referred to as an RIC regimen or treatment.

The blood flow restriction (or occlusion) typically takes the form of an applied pressure to the limb that is sufficient to occlude blood through the limb. In some instances, the occlusive blood pressure is above systolic pressure (i.e., supra-systolic pressure). It may be about 5, about 10, about 15, about 20, or more mmHg above (or greater than) systolic pressure. In some instances, the occlusive blood pressure may be at or below systolic pressure. Since systolic pressure will differ between subjects, the absolute pressure needed to induce ischemia will vary between subjects. In other embodiments the pressure may be preset at, for example, 200 mmHg. The blood flow restriction may be accomplished using any method or device provided it is capable of inducing transient ischemia and reperfusion, whether manually or automatically. Such devices include without limitation a manually inflatable cuff, or an automated device as described below. The devices comprise cuffs of standard width or cuffs of greater than standard width.

The induced ischemic period is transient. That is, it may have a duration of about 1, about 2, about 3, about 4, about 5, or more minutes. Similarly, the reperfusion period may have a duration of about 1, about 2, about 3, about 4, about 5, or more minutes.

One or both upper limbs or one or both lower limbs may be used although in some instances one or both upper limbs are preferred. In some instances, RIC is performed on two different sites on the body, in an overlapping or simultaneous manner.

Devices for performing RIC are also known in the art, and include those described in U.S. Pat. No. 7,717,855 and US Publication No. 2012/0265240 A1, both of which are incorporated herein by reference in their entirety. Both systems comprise a cuff configured to retract about a limb of a subject, an actuator connected to the cuff that when actuated causes the cuff to contract about the limb of the subject to reduce blood flow therethrough, and a controller that controls the actuator according to a treatment protocol. The treatment protocol typically includes a plurality of treatment cycles, each of which may comprise a cuff actuation period during which the actuator contracts the cuff about the limb of the subject to a pressure that occludes blood flow through the limb, an ischemic period during which the actuator maintains the cuff contracted about the limb at a set pressure point to occlude blood flow through the limb, a cuff release period during which the actuator releases the cuff to allow blood flow through the limb, and a reperfusion period during which the cuff is maintained about the limb in a relaxed state to allow blood flow through the limb.

Chronic RIC means performing a RIC regimen (which itself may comprise 1, 2, 3, 4, 5, or more cycles of ischemia and reperfusion) more than once over the course of more than one day. Chronic RIC encompasses daily performance of a RIC regimen, weekly performance of a RIC regimen, bi-weekly performance of a RIC regimen, monthly performance of a RIC regimen, including performance that is more or less frequent. Chronic RIC also encompasses performing a RIC regimen every other day, every third day, every fourth day, every fifth day, or every sixth day. The RIC regimens may be identical to each other or they may differ. Chronic RIC encompasses scheduled RIC regimens (e.g., non-random RIC regimens) or random RIC regimens (e.g., performing RIC when a subject feels the need rather than on a set schedule). Chronic RIC also contemplates that more than one RIC regimen may be performed on a single day.

SUMMARY

In one aspect, a device for performing remote ischemic conditioning includes an inflatable cuff configured to encircle the limb of a user, a cartridge containing a gas, a manifold providing fluid communication between the cartridge and the cuff, a first valve disposed between the cartridge and the cuff to control the flow of gas from the cartridge to the cuff, a second valve in fluid communication with the cuff which, when open, allows gas in the cuff to escape from the cuff, and a controller configured to open and close the first and second valve to regulate the flow of gas to and from the cuff to implement a remote ischemic conditioning treatment having at least one period of ischemia and one period of reperfusion. In one embodiment, the device includes a third valve in fluid communication with a cuff which is configured to open in response to an overpressure event. The device may also further include a pressure monitor, and the controller and pressure monitor may maintain a cuff pressure between preselected pressure limits during an ischemic period of the remote ischemic conditioning treatment. The cartridge may contain gas in a gaseous state or in a liquified state. Multiple cartridges may also be provided in other embodiments. Where multiple cartridges are employed, the number of cartridges may equal the number of cycles in the remote ischemic conditioning treatment. In another embodiment, the cartridge may contain chemicals which, when activated by the controller, react to produce gas. This chemical reaction may be initiated by sending a signal from the controller to the cartridge. In another embodiment, the device also includes a pressure monitor which senses pressure in the cuff and/or the manifold, and opens a third valve when the pressure in the manifold or in the cuff exceeds a predetermined value. The cartridge may be disposed in a housing on the cuff, or within the cuff.

In another aspect, a device for performing a remote ischemic conditioning protocol includes an inflatable cuff configured to encircle a limb of a user, a housing attached to the cuff, at least one cartridge containing a gas or a gas-producing material, a manifold disposed between the cartridge and the cuff to provide fluid communication between the cartridge and the cuff, at least one valve disposed between the cartridge and the manifold to control the flow of gas from the cartridge to the manifold, a second valve in fluid communication with the cuff and the manifold for allowing gas within the manifold and/or the cuff to escape therefrom when in an open condition, a controller configured to control the opening and closing of the first valve and the second valve to control the flow of gas to and from the cuff to permit the cuff to be inflated during an ischemic period and to be deflated during a reperfusion period as part of a remote ischemic conditioning treatment, and a battery to provide power to the controller. The housing may include a switch to initiate a remote ischemic conditioning treatment and the like to indicate the status of the treatment. The cartridge may contain gas in a liquified form. The cartridge may also contain chemicals which react to produce a gas. The chemical reaction may be initiated by an electrical pulse sent from the controller. The device in another embodiment may comprise multiple cartridges, each cartridge being associated with a different ischemic period of a remote ischemic conditioning treatment. The cartridges may be either disposed within the housing or within the cuff.

It should be appreciated that all combinations of the foregoing aspects and additional concepts discussed in greater detail below (provided such concepts are not mutually inconsistent) are contemplated as being part of the inventive subject matter disclosed herein.

The foregoing and other aspects, embodiments, and features of the present teachings can be more fully understood from the following description in conjunction with the accompanying drawings.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

The illustrative embodiments described herein are not necessarily intended to show all aspects of the invention. Aspects of the invention are not intended to be construed narrowly in view of the illustrative embodiments. It should be appreciated that the various concepts and embodiments introduced above and those discussed in greater detail below may be implemented in any of numerous ways, as the disclosed concepts and embodiments are not limited to any particular manner of implementation. In addition, it should be understood that aspects of the invention may be used alone or in any suitable combination with other aspects of the invention.

Many existing RIC devices rely on a battery to power a pump that inflates the cuff. The pump system used to inflate the cuff in these devices requires a considerable amount of power for operation. While some of the required power is for control purposes, the pump itself consumes the majority of the power. This high power consumption requires a fairly large battery pack. The combined size and weight of the pump and batteries may be substantial. Battery shelf life also is a concern. Shelf life is relatively limited, perhaps a year without charging or a few years without replacement. Battery powered devices are suitable when there are opportunities to charge the battery, such as in ambulances or in fixed, medically supervised locations. However, in an emergency or home use application, it would be desirable for the device to have a long shelf life, perhaps 10 years, be as compact as possible and not require an external charger. Similar requirements exist for an emergency RIC device available in public places (like emergency cardiac defibrillators (AED's)) such as in office buildings, in shopping malls and aboard aircraft. Field military use is another example where a rugged, compact, simple-to-use device with an extended shelf life would be highly desirable.

In one aspect of the invention, these requirements are met by eliminating the need for a pump and associated batteries to accomplish cuff inflation, resulting in a substantially smaller, lighter device with an increased shelf life.

In another aspect of the invention, additional electrical power requirements, that result from the illumination of a number of LEDs that indicate control functions, are obviated by reducing the LED count to a single LED indicating that the unit is active.

The present invention provides a non-electrically powered source of gas of sufficient capacity to complete the RIC cycle, thus obviating the need for an electromechanical air pump. One embodiment of such a source of gas is a small gas cartridge similar to those used in carbonation systems. This type of cartridge can be filled with a variety of gases including nitrous oxide (liquid phase), carbon dioxide (liquid phase), nitrogen (gas phase) and argon (gas phase). While liquid phase gases are somewhat more compact, gas phase systems such as nitrogen and argon have specific advantages. Being in a gas phase at the storage pressure eliminates the need to specifically orient the cartridge to prevent discharge of liquid into the control circuit, and to volatilize the liquid. As a result, the use of a gas phase cartridge allows for operation at lower ambient temperatures. Nitrogen and argon are desirable because they are inert and in gas phase at the storage pressures required to provide a reasonably compact reservoir. Either a single cartridge may be provided that has the gas capacity for all inflation cycles or multiple gas cartridges may be provided, one for each inflation cycle. For multiple cartridges, each is triggered at the start of an inflation cycle.

In another embodiment of the present invention, a non-electrically powered source of gas may include a cartridge that uses a chemical reaction to generate the gas pressure required to perform the RIC procedure. Either a single chemical reaction chamber cartridge may be provided with adequate capacity for all inflation cycles, or multiple cartridges may be provided, each having capacity for a single inflation cycle. For multiple cartridges, each is triggered at the start of an inflation cycle. The gas generation materials may be incorporated into the interior of the cuff bladder obviating the need for some control mechanisms. If the provided reaction chemicals produce gas in excess of that required to provide a single inflation of the cuff, a pressure release valve limits the inflation pressure to a desired value, such as 200 mmHg. A valve may be provided to release the pressure after the desired duration of cuff inflation. The inflation cycle of the cuff may be initiated by an electrical pulse from the controlling microprocessor. If the reaction generating the inflating gas volume is exothermic, adequate protection in the form of insulation or the like is provided to prevent injury to the user. Reactions similar to that used in inflating automotive airbags may be used to generate the gas required to inflate the cuff. Other chemical reactions that might be suitable are known to those skilled in the art.

In another aspect of the invention, further reduction in electrical power requirements may be achieved by simplifying the pneumatic control systems. Pressure control in the cuff may be achieved by the use of two magnetically latched valves, one to control the incoming gas pressure and one to provide venting. Magnetically latched valves require only a very brief current pulse (on the order of a millisecond) to change state from open to closed or closed to open. Once the state change has occurred, no application of current is required to maintain the state.

In yet another aspect, the requirement for a battery in the system may be completely eliminated. Some of the energy from the compressed gas may be utilized to generate electrical current to provide power to the microprocessor based control system and valving. A piezoelectric generator may be incorporated into the system to provide adequate power to provide logic and control functions.

In yet another aspect, the microprocessor control and electro-mechanical valving may be replaced with purely pneumatic logic. Flow and pressure control are managed with pneumatic logic incorporated into a micro-fluidic chip containing timing, pressure control and valving functions.

In yet another aspect, the device may include systems to prevent unintended activation of the device, as it is likely that for home emergency use, the device would be accessible to children or subject to rough treatment. In one embodiment a simple rotary switch may incorporate a squeeze-to-unlock feature similar to that used on many household chemical or drug containers.

In yet another aspect, connectivity to web based or other monitoring systems may be provided to alert emergency personnel that the device has been activated and that a medical emergency has occurred. A Bluetooth or Wi-Fi connection may enable such connectivity.

In yet another aspect, an audible alarm indicating activation of the device may be provided for home use. Either an electronic annunciator may be activated when the device is activated or a "whistle" may be provided by diversion of some of the gas available from the reservoir.

In yet another aspect, automatic activation of the device may be achieved when it is placed on the limb. Such activation may be achieved by positioning of the activation switch such that it achieves electrical or mechanical activation when the cuff is wrapped and locked into position on the limb.

The reduction in size and complexity provided by the aforementioned embodiments and the requirement of a single use permit a unitary construction wherein the cuff and inflation and control elements are provided in a preassembled format, and may be disposable.

Turning now to the figures, several embodiments are described in further detail.

Figure 1:
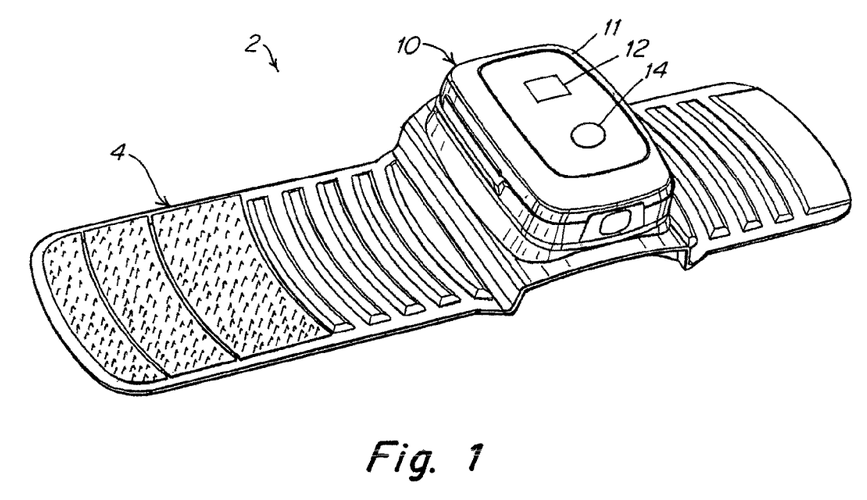
FIG. 1 is a perspective view of an assembled system for remote ischemic conditioning according to the present invention.

FIG. 1 illustrates one embodiment of a system 2 for RIC. System 2 includes an inflatable cuff 4 and a controller 10. In one embodiment, a housing 11 of controller 10 may be permanently attached to cuff 4 so that cuff 4 and controller 10 form a single unit. Housing 11 may be attached to cuff 4 in any known manner, such as by molding, glue, stitches, rivets, screws and the like. In one embodiment, housing 11 for controller 10 may be molded integrally with cuff 4. In these embodiments, typically, cuff 4 and controller 10 are designed for a single use, and are disposable once the use has completed. In other embodiments, controller 10 may be removably attached to cuff 4, such as shown in U.S. application Ser. No. 13/088,243 filed Apr. 15, 2011, which is herein incorporated by reference in its entirety. Also, in other embodiments, system 2 could include two or more cuffs and associated controllers which are the same as or different from cuff 4 and controller 10 and which could be used with the same limb as cuff 4 on different limbs of the same person.

Typically, controller 10 of this invention includes a button or switch 12 for stopping or starting an RIC treatment, and an indicator light 14 which indicates whether the treatment has been initiated, whether the treatment is in progress, or whether, when the light is not illuminated, the treatment has stopped. Light 14 typically is an LED. Both switch 12 and light 14 may be displayed on the front face of housing 11. Other control features, and other displays, may be used in conjunction with controller 10, such as lights indicating the progress of the treatment and providing an indication of the pressure, if desired.

Figure 2:
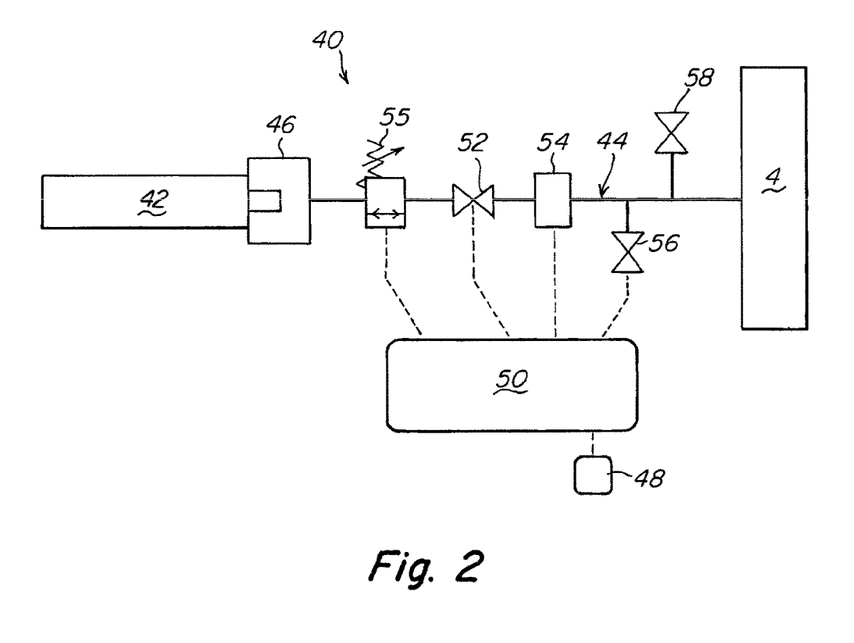
FIG. 2 is a schematic drawing illustrating one embodiment of a system having a single gas cartridge.
Figure 4:
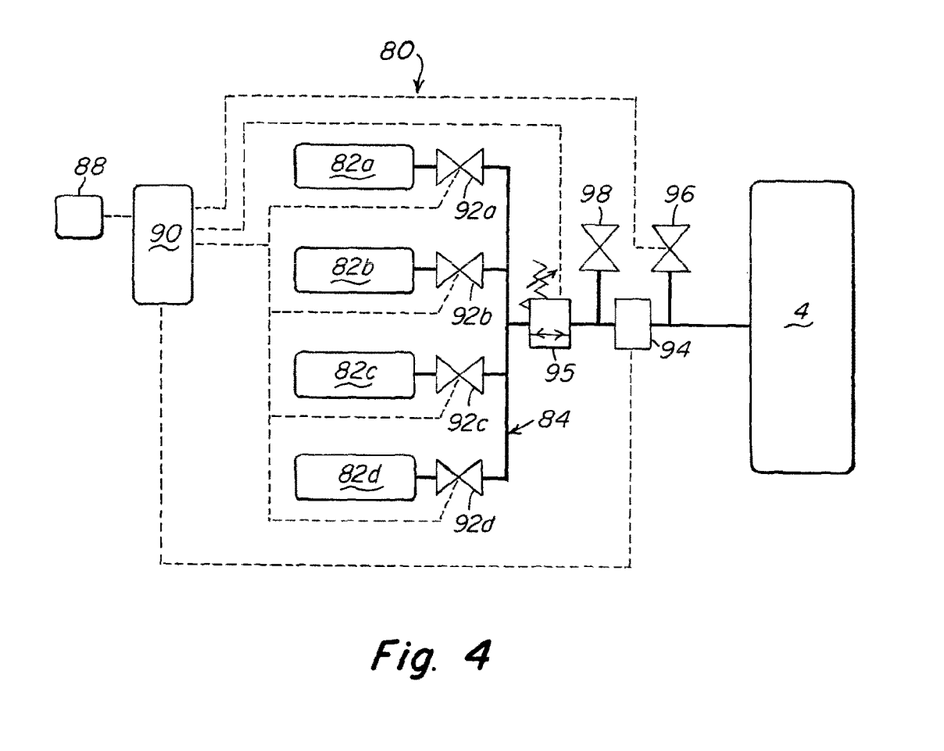
FIG. 4 is a schematic drawing illustrating one system having an embodiment of multiple gas cartridges.
Figure 5:
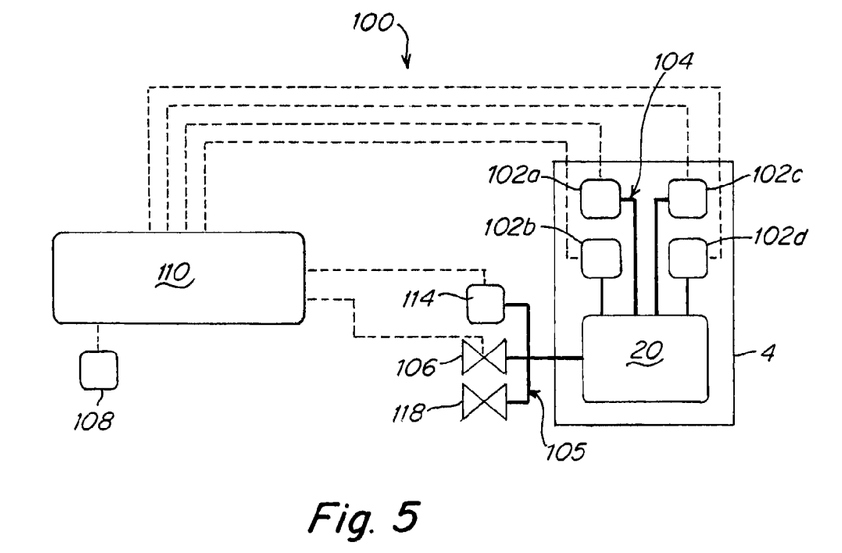
FIG. 5 is a schematic drawing illustrating one embodiment of a system having multiple chemical cartridges.
Figure 6:
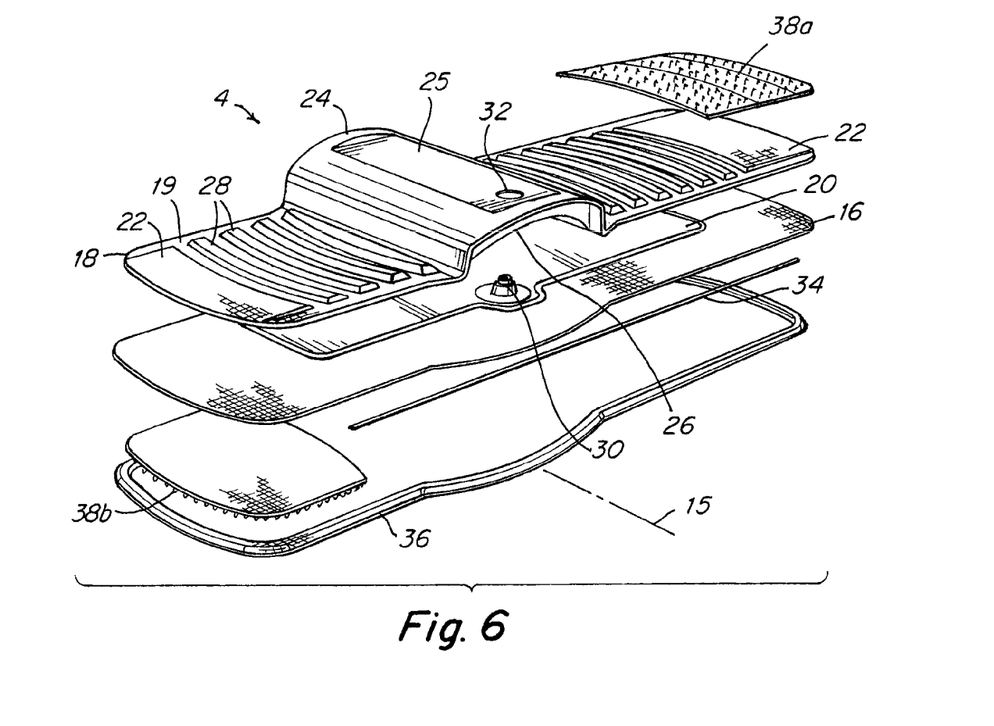
FIG. 6 is an exploded, schematic perspective view of the cuff of the system depicted in FIG. 1.

One aspect of this invention will now be described with particular reference to FIG. 2. FIG. 2 is a schematic drawing illustrating an embodiment of this aspect which utilizes a single gas cartridge for inflating cuff 4 for performing the RIC treatment. In FIGS. 2-5, dashed lines represent an electrical connection, while solid lines represent a gas line or manifold. Device 40 may include a single gas cartridge 42, a manifold 44, a coupler 46 for coupling gas from cartridge 42 to manifold 44, valves 52, 56 and 58 and a pressure monitor 54. Some embodiments may also include a pressure regulator 55. Manifold 44 is pneumatically coupled to a valve 30 in cuff 4 (see FIG. 6) which permits inflation of the bladder 20 in cuff 4 (FIG. 6). Device 40 also may include a power source, such as battery 48 and a suitably programmed microcontroller 50. Microcontroller 50 is programmed to control the operation of device 40. Battery 48 typically is a conventional dry cell, non-rechargeable battery, although battery 48 could be a rechargeable lithium ion battery or other suitable battery. Either a 6 volt, a 9 volt or a 12 volt battery may be used. One battery is preferred, although more than one battery may be used for some applications. Valves 52 and 56 are controlled by microcontroller 50. Valve 52 is opened when it is desired to inflate cuff 4 during an ischemic period, and is closed when cuff 4 is fully inflated. Valve 56 is opened when it is desired to deflate cuff 4 during a reperfusion period. Valves 52 and 56 may be magnetically latched valves. Such valves are preferred because they require less power from the battery. Only a very brief current pulse on the order of a millisecond is required to open or close the valve. Once the valve has been opened or closed, no application of current is required to maintain the valve in that open or closed state since the valve is maintained in its state using a magnetic latch. A commercially available example of such a valve is provided by The Lee Company, a Lee Series 120 Solenoid Valve.

There may be an additional safety valve 58. Valve 58 only opens when the pressure within the cuff 4 or within the manifold 44 exceeds a predetermined value for which valve 58 is set. So long as the pressure within the cuff 4 or within the manifold 44 remains within a desired range, safety valve 58 remains closed. Valve 58 is preferably a known mechanical valve, since it will open regardless of whether there is a battery failure or other current failure, but valve 58 may also be a magnetically latched valve, or any other suitable valve. If valve 58 is a magnetically latched valve, it would open in response to an condition measured by pressure monitor 54 and would be electrically connected to microprocessor 50 (not shown).

Cartridge 42 typically is a small gas cartridge similar to those used in carbonation systems. Cartridge 42 may be filled with nitrous oxide which typically is in a liquid phase, carbon dioxide which typically is in a liquid phase, nitrogen which typically is in a gas phase, or argon which is typically in a gas phase. Other suitable gases may also be used. In some embodiments, gas phase systems such as nitrogen and argon are preferred, since no specific orientation of the cartridges is required to prevent discharge of the liquid into the control circuit. Also, since the propellant is already in a gas phase, device 40 may be used at lower ambient temperatures, since heat is not required to convert the liquid into gas. In addition, the nitrogen and argon are inert and in gas phase at the storage pressures required to provide a reasonably compact reservoir. For example, a commercially available compressed argon cartridge (iSi group 4.5 gram, 14 ml water capacity) is approximately 18.6 mm in diameter and 83 mm in length. Such a cartridge has adequate volume to inflate the cuff 4 at least 5.8 times. This is more than adequate to perform a typical RIC treatment.

Conventional gas cartridges 42 may have extremely high gas pressures within. Such pressures could be of the order of 2-3000 pounds per square inch. With such cartridges, in some embodiments, a pressure regulator 55 may be positioned between cartridge 42 and valves 52 and 54 and cuff 4, to regulate the pressure in manifold 44 to protect valves 52 and 54 and cuff 4 from the effects of extreme pressures.

In operation, a medical professional, some other person or a user, wraps cuff 4 about the arm or leg of a person on whom the RIC treatment is to be performed (i.e., a user). Switch 12 is then pressed, which initiates the treatment. A signal is sent from the microcontroller 50 to valve 52, which opens in response and permits gas to escape from cartridge 42 through coupler 46, through manifold 44 and into bladder 20 through valve 30. Cuff 4 then inflates. During this time, valves 56 and 58 remain in a closed position. Pressure monitor 54 monitors the pressure in the manifold 44 and therefore in cuff 4. When the pressure reaches the level required to occlude blood flow in the person's limb (typically at or above systolic, although sub-systolic pressures could be used), microcontroller 50 closes valve 52. Valve 52 remains closed as do valves 56 and 58, until the ischemic period has been completed. This ischemic period is typically greater than one minute, may be five minutes, or may be greater than five minutes. The actual duration of the period depends on how the microcontroller is programmed, and the particular use for which device 40 is intended. Once the ischemic period is complete, microcontroller 50 opens valve 56 to permit the gas to escape from cuff 4 into the atmosphere. The microcontroller retains valve 56 in the open position during the reperfusion period for the duration programmed into the microcontroller. Typically, this duration is greater than a minute, may be five minutes, or greater than five minutes. Once the reperfusion period is complete, valve 56 is closed by microcontroller 50, and microcontroller 50 again opens valve 52 to repeat the cycle. This cycle may be repeated as many times as is programmed in the microcontroller, and for which there is gas available in cartridge 42. In a typical RIC treatment, there are 4 cycles of alternating ischemia and reperfusion, although greater or fewer numbers of cycles may be used.

If at any time during a treatment there is a system failure which causes an condition that exceeds the pressure for which safety valve 58 is set, valve 58 may open to prevent any injury to the user. Such an condition may be caused by a battery failure or blockage in relief valve 56. Another possible cause of an condition is a failure of valve 52 such that it does not close when the desired pressure has been reached in cuff 4 or in manifold 44. If valve 58 is a mechanical valve, it does not depend on battery power to open, and will open even if there is a battery failure.

In this embodiment, all of cartridge 42, manifold 44, coupler 46, valves 52, 56 and 58, pressure monitor 54, battery 48 and microcontroller 50 may be contained within housing 11 of controller 10. However, it should be understood, that certain of these elements could be outside housing 11. For example, cartridge 42 could be placed on or within cuff 4 in direct communication with bladder 20 in cuff 4. Such placement would be particularly desirable where controller 10 is detachable from cuff 4 so that cuff 4 may be disposable, and controller 10 may be reusable for a second procedure.

Figure 3:
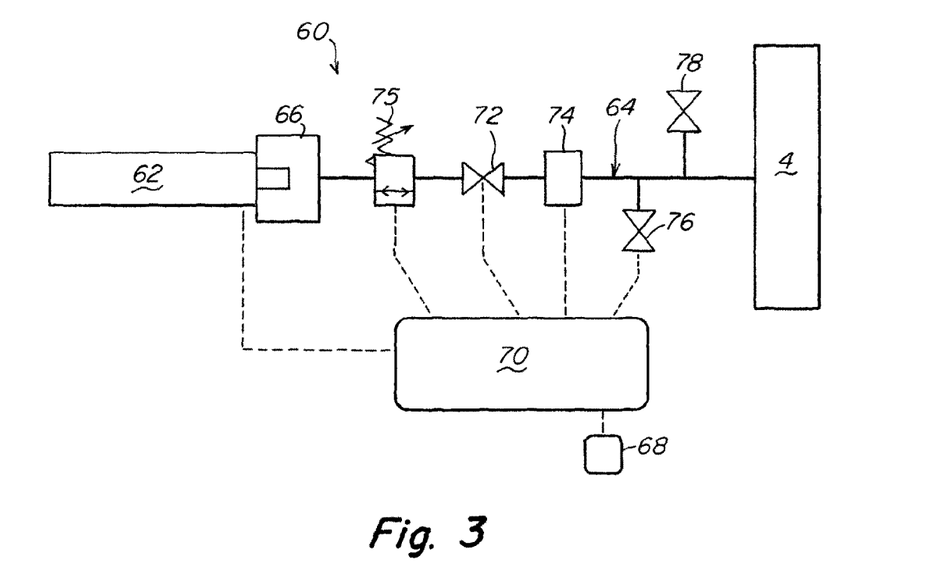
FIG. 3 is a schematic drawing illustrating one embodiment of a system having a single chemical cartridge.

Another embodiment of this aspect of the invention will now be described with reference to FIG. 3. In FIG. 3, device 60 may include a single gas generation cartridge 62, a manifold 64, a coupler 66, a battery 68, a microcontroller 70, valves 72, 76 and 78 and a pressure monitor 74. Some embodiments may also include a pressure regulator 75 for the reasons previously discussed with respect to pressure regulator 55. Device 60 is similar to device 40 except that gas generation cartridge 62 contains chemicals, that when activated, produce a chemical reaction that generates the gas necessary to inflate bladder 20 of cuff 4. Coupler 66 couples the outlet from cartridge 62 to valve 72. Valve 72, when open, communicates with manifold 64 which communicates with bladder 20 of cuff 4 through valve 30 to inflate cuff 4. Pressure monitor 74 monitors the pressure in manifold 44 and cuff 4. Valve 76 is opened when it is desired to deflate cuff 4, typically during a reperfusion period. Valve 78 is a safety valve which opens during an over-pressure event to prevent any injury to a user. Microcontroller 70 controls the operation of valves 72 and 76, while battery 68 provides the necessary current to run microcontroller 70 and to open and close valves 72 and 76. In this embodiment, battery 68 may also provide the current necessary to initiate the chemical reaction in gas generation cartridge 62. Valves 72 and 76 may be magnetically latched valves, while valve 78, like valve 58, may be a mechanical relief valve, or a magnetically latched valve or any other suitable valve.

Gas generation cartridge 62 may include any of a number of compounds that react to produce the required volume of gas. Cartridge 62 may contain a single chemical reaction chamber, or multiple reaction chambers. For multiple chambers, one chamber is triggered at the start of each inflation cycle for an ischemic period. In either embodiment, should the amount of gas that is produced be in excess of what is required to inflate cuff 4 to the desired pressure, it may be released through safety valve 78. If the reaction generating the gas is exothermic, steps must be taken to insulate the cartridge from the user to prevent injury to the user by providing insulation around cartridge 62.

In one embodiment, chemicals used in automotive air bag gas generators may be used to generate the gas required to inflate cuff 4. Reactions used in known air bag gas generators produce a sufficient amount of nitrogen gas for RIC treatments. In one example, a mixture of $NaN_3$, $KNO_3$, and $SiO_2$ may be used in cartridge 62. A series of three chemical reactions inside cartridge 62 to produce nitrogen gas to inflate cuff 4. The reactions may be initiated by an electrical charge or pulse from battery 68 which ignites the mixture. The resulting chemical reaction creates the high temperature condition necessary for $NaN_3$ to decompose and release nitrogen gas. The $KNO_3$ and $SiO_2$ remove the sodium metal, which is a potentially harmful byproduct of the decomposition of $NaN_3$, by converting the sodium metal to a harmless material. First, the sodium metal reacts with potassium nitrate ($KNO_3$) to produce potassium oxide ($K_2O$), sodium oxide ($Na_2O$) and additional nitrogen gas. This additional nitrogen gas can also be used to inflate cuff 4. The foregoing metal oxides react with silicon dioxide ($SiO_2$) in a final reaction to produce silicate glass which is harmless and stable, and can readily be discarded.

In another embodiment, hydrogen peroxide may be used to generate oxygen gas as the hydrogen peroxide decomposes into oxygen and water in cartridge 62 in the presence of a catalyst.

Operation of this embodiment of device 60 is similar to the operation of device 40. First, cuff 4 is wrapped about the arm of a user. To initiate an RIC cycle, the user presses switch 12, which causes light 14 to be illuminated on controller housing 11. Switch 12 causes an electrical pulse to be sent to cartridge 62 which initiates the reaction just described above. When the gas is generated, microcontroller 70 opens valve 72. The gas emitted from gas generation cartridge 62 passes through coupler 66, and valve 72 into manifold 64. Thereafter, gas passes into bladder 20 of cuff 4 through valve 30. Valves 76 and 78 remain closed during this time. When pressure monitor 74 determines that the pressure in manifold 64 and cuff 4 is at the proper level to occlude blood flow, valve 72 is closed, and the pressure is maintained in cuff 4 at the desired level for the ischemic period. Once the ischemic period has expired, valve 76 is opened by microcontroller 90 and the gas is vented to the atmosphere during the reperfusion period. The cycle is then repeated as discussed above until the number of predetermined cycles of RIC programmed in microcontroller 70 have been performed. Typically, four such cycles are performed with ischemic and reperfusion periods of greater than a minute, five minutes, or greater than five minutes. Valve 78 will open automatically if the pressure in manifold 64 or cuff 4 exceeds a desired level.

Another embodiment of this aspect will now be described with respect to FIG. 4, which is a schematic drawing of a device 80 employing multiple gas cartridges. Device 80 includes cartridges 82a-d, valves 92a-d, valves 96 and 98, pressure monitor 94, manifold 84, microcontroller 90 and battery 88. In some embodiments, device 80 may also include a pressure regulator 95 for the reasons already discussed with respect to pressure regulator 55. Device 80 typically, but not necessarily, includes one gas cartridge for each cycle of the RIC treatment. For purposes of illustration, it is assumed that the RIC treatment includes four cycles of ischemia and reperfusion of approximately 5 minutes each, however, it should be understood that more or fewer cycles of greater or shorter duration may also be used. In this illustrative embodiment, there are four gas cartridges, 82a, 82b, 82c and 82d. Each cartridge 82a, 82b, 82c and 82d may be the same as cartridge 42 of device 40 except that cartridges 82a-d may be smaller and have a smaller gas capacity as each is needed only to supply gas for one ischemic period. Each cartridge has an associated corresponding valve 92a, 92b, 92c and 92d. Valves 92a, 92b, 92c and 92d are coupled by a manifold 84 to valve 30 of bladder 20. Each of valves 92a, 92b, 93c and 92d may be a magnetic latched valve, as described above, or may be any other suitable valve. There is also a relief valve 96 which, when opened by microcontroller 70, allows gas to escape from cuff 4 during each reperfusion period. Valve 96 may also be a magnetically latched valve, or any other suitable valve. Finally, there is a safety valve 98 which serves as a relief valve should excess pressure occur in the cuff or in the manifold 84. Preferably, valve 98 is a mechanical valve, although, like valve 58, valve 98 may be a magnetically latched valve or any other suitable valve.

In this embodiment, all of cartridges 82a-d may be contained within housing 11 of controller 10, or, in an alternative embodiment, the cartridges may be mounted internally to or on the surface of cuff 4. If cartridges 82a-d are mounted in or on cuff 4, manifold 84 also may be mounted on cuff 4.

In operation, cuff 4 is wrapped about the limb of a user, and switch 12 is depressed, illuminating light 14. In response, microcontroller 90 sends a signal to open valve 92a, releasing gas from cartridge 82a into manifold 84 which then conducts the gas to bladder 20 via valve 30 of cuff 4, initiating the first ischemic period. Once the appropriate pressure is measured by pressure monitor 94, valve 92a is closed by microcontroller 90 and remains closed during the first ischemic period to occlude blood flow in the limb. After the appropriate time has passed, say, for example, greater than one minute, five minutes, or greater than five minutes, valve 96 is opened by a signal from microcontroller 90, and the gas is exhausted from cuff 4 for the duration of the reperfusion period, which typically is greater than one minute, five minutes, or greater than five minutes. At the end of the first reperfusion period, valve 96 is closed by a signal from microcontroller 90, and valve 92b is opened by microcontroller 90, releasing gas into cuff 4. This process is repeated for each cycle in the RIC treatment, by sequentially opening and closing valves 92b, 92c and 92d for each cycle. Valve 96 is opened to exhaust the gas from cuff 4 at the completion of the RIC treatment. Valve 98 serves as a relief valve should an over-pressure condition occur in manifold 84 or cuff 4.

Yet another embodiment of this aspect of this embodiment will now be described with respect to FIG. 5, which includes multiple chemical gas cartridges, typically one cartridge for each period of ischemia. For purposes of illustration only, FIG. 5 shows four cartridges for four periods of ischemia and reperfusion. However, it should be understood that there may be more or fewer periods of ischemia and reperfusion and therefore more or fewer cartridges.

Device 100 includes chemical gas cartridges 102a, 102b, 102c and 102d. Cartridges 102a, 102b, 102c, and 102d are shown in FIG. 5 to be embedded within cuff 4. However, it is to be understood that cartridges 102a-d instead may be disposed within housing 11, as shown for device 80 in FIG. 4, or attached to the exterior of cuff 4. If cartridges 102a-d are embedded within or attached to cuff 4, insulation (not shown) may be deployed about the cartridges to prevent injury to the user. In FIG. 5, each cartridge 102a-d is in direct gas communication with the interior of bladder 20 in cuff 4 through valve 30. Device 100 also includes valves 106 and 118, pressure monitor 114, manifolds 104 and 105, microprocessor 110 and battery 108. As each cartridge 102a-d is selectively activated, gas is fed directly to bladder 20 by manifold 104. Although not shown, a valve and a pressure regulator could be installed between each cartridge 102a-d and bladder 20 to protect against uncontrolled or high pressures, but such valves and regulators may not be necessary when the cartridges are embedded within cuff 4. Valve 106, which is also coupled to bladder 20 of cuff 4 by second manifold 105, allows release of gas from cuff 4 upon a signal from microprocessor 110. Valve 106 typically is a magnetically latched valve as discussed previously, although other electrically actuated or mechanically actuated valves may be used. Safety valve 118 and pressure monitor 114 are also coupled to manifold 105. Valve 118 serves to release any over-pressure that may occur in bladder 20 of cuff 4 or manifold 105. Valve 118 may be a mechanical valve, or like valve 58, may be a mechanically latched valve or any other suitable valve. Each cartridge 102a, 102b, 102c and 102d may be identical to cartridge 62 in device 60, except that cartridges 102a, 102b, 102c and 102d may be smaller and have less capacity, and they require no valves or couplers. Cartridges 102a-d may contain the same chemicals used to produce gas as previously described with regard to cartridge 62.

In operation, as in the other embodiments, the RIC treatment is initiated by actuating switch 12, which illuminates light 14. In response, microcontroller 110 sends an electrical signal to cartridge 102a which initiates the chemical reaction to produce the necessary gas. The gas is conducted by manifold 104 to bladder 20 in cuff 4. Cuff 4 is inflated and is maintained in the inflated condition for the ischemic period, which may be greater than one minute, five minutes or greater than five minutes. Pressure in cuff 4 is regulated by valve 106 in response to a pressure measured by pressure monitor 114. If too great a pressure is measured by pressure monitor 114, microcontroller 110 opens valve 106 to reduce the pressure. At the end of the ischemic period, valve 106 is opened, releasing gas from cuff 4. At the end of the reperfusion period which typically is greater than one minute, five minutes, or greater than five minutes, valve 106 is closed by microcontroller 110, and a signal is sent by microcontroller 110 to cartridge 102b to initiate a chemical reaction to produce gas for the second ischemic period of the treatment. The same process for cartridge 102a is repeated for cartridges 102b, 102c and 102d.

In another aspect, an embodiment of cuff 4 will now be described with respect to FIG. 6. Cuff 4 may be axially rigid while being soft or non-irritating to the skin. Cuff 4 may include an inner layer 16, a layer 18, and at least one selectively inflatable bladder 20 disposed between layers 16 and 18, as depicted in FIG. 6. In other embodiments, multiple bladders 20 may be employed. Cuff 4 may be adapted to encircle a limb of a user. Axis 15 represents the approximate center of a circular configuration formed when cuff 4 is wrapped about a user's limb. An axial direction of cuff 4 corresponds to the approximate direction of axis 15. Cuff 4 has a longitudinal direction extending down the length of cuff 4 which is substantially perpendicular to the above defined axial direction. Cuff 4 may also be intended to be a disposable item for use with a removable or non-removable controller 10. Inner layer 16 typically is positioned adjacent to, and often in contact with, the skin of a user. Since inner layer 16 may be in contact with skin, the inner layer may be made from a soft and/or non-irritating material. Inner layer 16 may be made from a knit, woven, or felted cloth. The cloth may include either natural or synthetic materials. Possible cloths include brushed polyester, brushed nylon, and/or other suitable materials as would be apparent to one of skill in the art. Alternatively, inner layer 16 may be made from a foam. In some embodiments, inner layer 16 may be further adapted to provide moisture absorption, wicking, and/or breathability to cuff 4.

In some embodiments, cuff 4 may include two sections 22 spaced apart in a longitudinal direction and an intermediate section 24 disposed between sections 22. Intermediate section 24 may be constructed to have a greater rigidity than sections 22. The increased rigidity of the intermediate section 24 may be created either by an inherent material property difference, a difference in the physical construction (e.g. a thicker section and/or inclusion of reinforcing features), or both. In one embodiment, intermediate section 24 may include a substantially flat outer surface 25 for attachment to controller 10. Intermediate section 24 may also include an inner surface 26 which is curved in the longitudinal direction of the cuff 4. The curved inner surface 26 may be constructed so as to generally conform to the curvature of a limb. In some embodiments, the size and curvature of the cuff 4 may be suited for a variety of sizes and ages of patients ranging from neonates to obese adults. Cuff 4 may also be sized for attachment either to an arm or a leg. Intermediate section 24 may be constructed from thermosetting plastics, thermoforming plastics, and/or foamed materials. Sections 22 and intermediate section 24 may be integrally formed with one another, or they may be formed separately and subsequently joined using any appropriate method including, but not limited to, a sewn seam, ultrasonic welds, adhesives, rivets, clamping structures, and/or mechanically interlocking features. Section 22 may be formed of a foam material or any other suitably flexible yet strong material.

In one embodiment, cuff 4 may also include a plurality of reinforcing structures 28 substantially aligned in the axial direction of the cuff assembly. Reinforcing structures 28 typically may be formed in outer layer 18 of sections 22. Reinforcing structures 28 provide axial rigidity to the cuff 4. The increased axial rigidity provided by reinforcing structures 28 helps to distribute the pressure applied by cuff 4 in the axial direction to provide a substantially uniform pressure across the axial width of the cuff 4. Reinforcing structures 28 may also help to prevent kinks in cuff 4 when it is placed around the arm or leg of a user. Reinforcing structures 28 may be spaced apart in a longitudinal direction to permit the cuff 4 to easily bend around an encircled limb while still providing increased axial rigidity. Reinforcing structures 28 may be curved or straight in shape in the axial direction. In some embodiments, the reinforcing structures 28 may be integrally formed with the foam in sections 22 such as by the application of heat and/or pressure (e.g. thermoforming) to selectively melt and/or compress portions of the foam in sections 22. The uncompressed and/or unmelted portions of foam in sections 22 form the raised reinforcing structures 28. Alternatively, reinforcing structures 28 may be separately formed and subsequently joined to sections 22.

Layer 18 may also include a cloth layer 19 applied to an exterior surface. Cloth layer 19 may be formed of a low stretch or non-stretch cloth. The low stretch or non-stretch properties may be an inherent property of the cloth selected. Alternatively, cloth layer 19 may be a made from thermoformable materials and may be laminated to the exterior surface of layer 18. The lamination process may alter the thermoformable fabric to be a low stretch or non-stretch material. In one embodiment, the cloth may be applied to and laminated with layer 18 in a flat layout prior to forming reinforcing structures 28. Reinforcing structures 28 may subsequently be thermoformed to a final desired shape. The resulting sections 22 may be soft and have low stretch or non-stretch properties. Furthermore, sections 22 may be thermoformable enabling subsequent processing steps.

Selectively inflatable bladder 20 may be disposed between inner layer 16 and layer 18. Bladder 20 may have a valve 30 arranged and adapted to provide a fluid inlet to the interior of bladder 20. Valve 30 extends through a hole 32 in the intermediate section 24 of cuff 4. Valve 30 may be placed in sealed fluid communication with corresponding manifolds 44, 64, 84 and 104 of respective devices 40, 60, 80 and 100. Valve 30 may provide pressurized gas to bladder 20. In some embodiments, bladder 20 may be a component separate from layers 16 and 18. Bladder 20 may be formed such as by bonding two separate sheets of thermoplastic polyurethane together. In other embodiments, bladder 20 may be formed from air impermeable layers incorporated into layers 16 and 18 of cuff 4. Layers of bladder 20 may be bonded together in an air tight manner using any number of methods including adhesives, ultrasonic welding, beads of material around the edges, and/or other appropriate methods as would be apparent to one of skill in the art. Bladder 20 may also be formed as a unitary structure without separate layers.

Layers 16, 18, 19, and bladder 20 of cuff 4 may be held together at their edges in any suitable fashion, such as by a binding material 36 wrapped around the edge of cuff 4 and sewn to cuff 4, as shown in FIG. 6. Alternatively, cuff 4 may be held together using adhesives, rivets, ultrasonic welds, or other appropriate methods as would be apparent to one of skill in the art.

In one aspect, it may be desirable to provide a non-slip interface to prevent cuff 4 from moving on the limb of a user, since cuff 4 may be worn for protracted periods of time. To provide a non-slip interface, at least one non-slip structure 34 may be disposed on the face of inner layer 16. The non-slip structure 34 may be printed, glued, sewn, applied as a bead of material using a guided tool, or by hand. The non-slip structure 34 may include, but is not limited to, one or more strips of silicone.

Cuff 4 may also include fasteners to hold the cuff on a limb of a user and to adjust the circumferential size of the cuff 4 when in the fitted state. Such fasteners include, but are not limited to, hook and loop fasteners, latches, ratchet mechanisms, clasps, snaps, buckles, and other appropriate structures as would be apparent to one of skill in the art. For example, the fastener may be a hook and loop fastener including a plurality of adjacent unconnected hook sections 38a disposed on layer 18 or 19 and loop sections 38b disposed on inner layer 16. Hook sections 38a may extend in the axial direction of the cuff 4. The width of each hook section 38a, with respect to the longitudinal direction of the cuff, may be selected to provide a flexible cuff able to wrap around different sized limbs.

In another embodiment, cuff 4 may be provided as a closed, elastic circular sleeve that may be slid over an arm or leg to the appropriate position. In such an embodiment, no fasteners, such as sections 38a and 38b would be necessary. Such an embodiment may include one or more elastic sections or bands to retain the cuff on limbs of varying size.

In another aspect, instead of a battery in the foregoing devices 40, 60, 80 and 100, a piezoelectric generator may be provided. This piezoelectric generator may be powered by diverting some of the compressed gas either from the gas cartridges, or from the chemical cartridges. In addition, gas diverted from either the chemical cartridges or the gas cartridges could be used to generate a whistle or other like sound to indicate to the user when the device is functioning. Such a whistle could be used to replace light 14. Finally, the microcontroller and the electromechanical valving may be replaced entirely with pneumatic logic. Flow and pressure control could be managed with pneumatic logic incorporated into a microfluidic chip containing timing, pressure control and valving functions.

Each of devices 40, 60, 80 and 100 may have additional features. For example, microcontrollers 50, 70, 90 and 110 may also determine blood pressure during, or as part of, an RIC treatment protocol. Microcontrollers 50, 70, 90 and 110 may be programmed with certain error conditions which may cause the procedure to be aborted. These error conditions may include, but are not limited to: the cuff 4 is not pressurized within a predefined period, such as 20 seconds, 30 seconds, 40 seconds, 50 seconds, or one minute; there is no communication between the microcontroller and the valves upon start up; there is no communication between the microcontroller and the valves for more than a predefined period, such as two, three, four, or five seconds; cuff pressure is not maintained; a cartridge continues to emit gas after a predefined period; pressure in cuff 4 is not near zero gage pressure within a predefined period, such as 20 seconds, 30 seconds, 40 seconds, 50 seconds, or one minute after the end of an ischemic period; pressure in cuff 4 is above a predetermined pressure such as 200, 220, 240 or 260 mmHg for longer than a predefined period, such as 5, 10, 20, or 30 seconds; and a cartridge does not respond after a command is sent to it by the microcontroller. The error condition may be cleared and/or the system may be reset such as by pressing switch 12 on the face of controller 10.

In some embodiments, the control circuit of a microcontroller 50, 70, 90 and 110 may be programmable by a health professional and/or an end user according to a prescribed treatment protocol. Alternatively, the control circuit may only be programmed at the factory and may not be altered afterwards by the end user. The control circuitry may also include non-volatile memory for the logging and storage of treatment history. A health care professional may be able to access this memory to determine the treatment history of a user and determine compliance with a prescribed treatment regime. In another embodiment, the microcontroller may send this information via wireless, or hard wired, communication or by the internet to a separate receiver for patient records, monitoring, or call center purposes. In one embodiment, controller 10 may include a stop button. In some embodiments, the stop button and switch 12 may be incorporated into a single button or switch. Controller 10 may also include a hard wired and/or emergency stop button. In other embodiments, other controls may be included to allow expanded control of an RIC treatment.

In addition, controller 10 may include displays related to the current cycle, the number of cycles left in a treatment, whether the treatment is completed, error signals, charge of the battery, and other relevant information. In one embodiment, controller 10 may include a cycle time display that may indicate the remaining portion of the ischemic and reperfusion periods by using illuminated indicators arranged in a circular pattern corresponding to a full cycle. Each indicator of the time display may correspond to a set fraction of the ischemic and/or reperfusion period. When all of the indicators of cycle time display are illuminated, the cycle is complete. Alternatively, the indicators of cycle time display may start a cycle fully illuminated and sequentially turn off as the cycle proceeds. When each indicator of cycle time display is dark, the particular cycle is complete. Cycle time display could also be arranged in other linear, or non-linear, shapes corresponding to a full cycle. Controller 10 may also include a current cycle display, or a digital numeric display, indicating whether the current cycle is the first, second, third, or other cycle. A procedure complete indicator may be illuminated with a solid color or it may blink when the RIC treatment is complete to indicate the end of the procedure. An error display may indicate when an error has occurred by blinking or being fully illuminated. Alternatively, an error display may blink in a preset pattern or display a particular color to indicate which error has occurred.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A device for remote ischemic conditioning comprising:
   an inflatable cuff configured to encircle a limb of a user;
   multiple cartridges fluidly coupled to the cuff at one time for providing a source of gas to the cuff;
   a manifold providing fluid communication between all of the cartridges and the cuff;
   a plurality of first valves disposed between the cartridges and the cuff to control a flow of gas from the cartridges to the cuff, each first valve being associated only with a respective one of the cartridges, each first valve being selectively opened or closed to control a flow of gas only from its respective cartridge;
   a second valve in fluid communication with the cuff which, when opened, allows gas in the cuff to escape from the cuff; and
   a controller configured to selectively open the first valves to permit a flow of gas from each respective cartridge in a desired sequence to the cuff to implement a remote ischemic conditioning treatment having more than one cycle, each cycle having at least one period of ischemia and one period of reperfusion;
   wherein each cartridge is associated with a different cycle in the remote ischemic conditioning treatment to produce ischemia during an ischemic period.

2. The device of claim 1, further comprising a third valve disposed in fluid communication with the cuff and configured to open in response to an over-pressure event.

3. The device of claim 2, further comprising a pressure monitor which senses the pressure in the cuff and/or in the manifold, and opens the third valve when the pressure in the manifold or in the cuff exceeds a predetermined value.

4. The device of claim 1, further comprising a pressure monitor and wherein the controller and pressure monitor maintain a cuff pressure between preselected pressure limits during an ischemic period of the remote ischemic conditioning treatment.

5. The device of claim 1, wherein the cartridges contain a gas in a gaseous state.

6. The device of claim 1, wherein the cartridges contain a gas in a liquified state that transforms into a gaseous state upon release from the cartridges.

7. The device of claim 1, wherein the cartridges contain chemicals which, when activated by the controller, react to produce gas.

8. The device of claim 7, wherein a chemical reaction is initiated by sending a signal from the controller to the cartridges.

9. The device of claim 1, wherein all of the cartridges are disposed at one time in a housing on the cuff.

10. The device of claim 1, wherein all of the cartridges are is disposed at one time in the cuff.

11. The device of claim 1, wherein there is no battery that provides electrical power to the controller.

12. The device of claim 11, further comprising a piezoelectric generator for providing electrical power to the controller.

13. The device of claim 12, wherein the piezoelectric generator is powered by diverting gas from one of the cartridges to the generator.

14. The device of claim 1, further comprising a whistle that generates a sound resulting from gas being diverted from one of the cartridges to the whistle.

15. The device of claim 11, wherein the controller and at least one of the first and second valves includes pneumatic logic powered by gas diverted from one of the cartridges.

16. A device for performing a remote ischemic conditioning protocol, the device comprising;
   an inflatable cuff configured to encircle a limb of a user;
   a housing attached to the cuff;
   multiple cartridges fluidly coupled to the cuff at one time and containing a gas or a gas-producing material;
   a manifold disposed between the cartridges and the cuff to provide fluid communication between the cartridges and the cuff;
   a plurality of first valves disposed between the cartridges and the manifold to control a flow of gas from the cartridges to the cuff, each first valve being associated only with a respective one of the cartridges, each first valve being selectively opened or closed to control a flow of gas only from its respective cartridge;

a second valve in fluid communication with the cuff and the manifold for allowing gas within the manifold and/or the cuff to escape therefrom when in an open condition;

a controller configured to selectively control the opening and closing of the first valves to permit a flow of gas from each respective cartridge in a desired sequence to the cuff to permit the cuff to be inflated during an ischemic period as part of a remote ischemic conditioning treatment; and a battery to provide power to the controller.

17. The device of claim 16, wherein the housing includes a switch to initiate a remote ischemic conditioning treatment and a light to indicate the status of the treatment.

18. The device of claim 16, wherein the cartridges contain a gas in a liquid form.

19. The device of claim 16, wherein the cartridges contain chemicals which react to produce gas.

20. The device of claim 19, wherein a chemical reaction is initiated by an electrical pulse sent from the controller.

21. The device of claim 16, wherein all of the cartridges are disposed at one time within the housing.

22. The device of claim 16, wherein all of the cartridges are disposed at one time within the cuff.

* * * * *

UNITED STATES PATENT AND TRADEMARK OFFICE
CERTIFICATE OF CORRECTION

PATENT NO. : 10,213,206 B2  
APPLICATION NO. : 14/774009  
DATED : February 26, 2019  
INVENTOR(S) : Rocky Eugene Ganske et al.

Page 1 of 1

It is certified that error appears in the above-identified patent and that said Letters Patent is hereby corrected as shown below:

In the Claims

In Claim 10, at Column 16, Line 42, "is disposed at one time in the cuff.", should read -- disposed at one time in the cuff. --

Signed and Sealed this  
Twenty-third Day of April, 2019

Andrei Iancu  
*Director of the United States Patent and Trademark Office*